United States Patent
Stoer et al.

(10) Patent No.: US 9,993,000 B2
(45) Date of Patent: Jun. 12, 2018

(54) ISOSORBIDE ETHER DERIVATIVES WITH PRESERVATION ACTIVITY

(71) Applicant: BASF SE, Ludwigshafen (DE)

(72) Inventors: Claudia Stoer, Duesseldorf (DE); David Melchior, Bergisch-Gladbach (DE); Claus Nieendick, Krefeld (DE); Annette Mehling, Wuppertal (DE); Thomas Albers, Duesseldorf (DE)

(73) Assignee: BASF SE, Ludwigshafen (DE)

( * ) Notice: Subject to any disclaimer, the term of this patent is extended or adjusted under 35 U.S.C. 154(b) by 0 days. days.

(21) Appl. No.: 15/559,440

(22) PCT Filed: Mar. 31, 2016

(86) PCT No.: PCT/EP2016/057088
§ 371 (c)(1),
(2) Date: Sep. 19, 2017

(87) PCT Pub. No.: WO2016/156505
PCT Pub. Date: Oct. 6, 2016

(65) Prior Publication Data
US 2018/0077936 A1    Mar. 22, 2018

(30) Foreign Application Priority Data

Apr. 1, 2015  (EP) .................................... 15162176

(51) Int. Cl.
*A01N 43/90*  (2006.01)
*C11D 3/48*  (2006.01)

(52) U.S. Cl.
CPC ................ *A01N 43/90* (2013.01); *C11D 3/48* (2013.01)

(58) Field of Classification Search
None
See application file for complete search history.

(56) References Cited

U.S. PATENT DOCUMENTS

2014/0315996 A1  10/2014  Pilz et al.
2014/0329870 A1  11/2014  Pilz et al.

FOREIGN PATENT DOCUMENTS

EP          2295030 A1    3/2011
WO    WO-2013041388 A1    3/2013

OTHER PUBLICATIONS

International Search Report and Written Opinion, International Application No. PCT/EP2016/057088, dated Jun. 7, 2016.

*Primary Examiner* — Karl J Puttlitz
(74) *Attorney, Agent, or Firm* — Marshall, Gerstein & Borun LLP

(57) ABSTRACT

Isosorbide mono ether derivatives with preservation activity.

19 Claims, No Drawings

ISOSORBIDE ETHER DERIVATIVES WITH PRESERVATION ACTIVITY

CROSS-REFERENCE TO RELATED APPLICATIONS

This application is the U.S. National Phase of PCT/EP2016/057088, filed Mar. 31, 2016, which claims the benefit of European Patent Application No. 15162176.0, filed Apr. 1, 2015.

FIELD OF THE INVENTION

The present invention relates to isosorbide ether derivatives suitable to enhance storage stability or the preservation of compositions, in particular liquid compositions, like detergents or cosmetic. The present invention is further related to isosorbide ether derivatives to boost the activity of specific preservatives

BACKGROUND OF THE INVENTION

Isosorbide derivatives are well known and used in many applications, like in detergents or cosmetic applications. Typically said substance class is used as a thickener or emulsifiers. For instance EP 2 295 030 A1 and WO 2013/041388 A1 describe isosorbide derivatives as suitable additives, like as thickener, emulsifiers etc.

Compositions must comply with several requirements depending on the end applications. For instance cosmetic compositions must have dermatological compatibility and good sensory impression. A further demand for compositions, especially for liquid compositions, is their storage stability. Storage stability can be enhanced due to different additives. One option is for instance the use of preservatives, like antimicrobials. Unfortunately known ester function containing preservatives are quite instable and thus have only limited storage stability function. Further its antimicrobial activity is rather low. However, low antimicrobial activity means that rather high amounts of antimicrobial must be present in the composition which causes undesired side effects.

Thus it is the object of the present invention to provide new preservatives having a high antimicrobial activity or boost the activity of known preservatives, or to increase the storage stability of compositions, like for detergents, cosmetic compositions and pharmaceutical compositions.

The finding of the present invention is that a specific class of isosorbide ether derivatives, namely those defined by formula (I) of the present invention show high antimicrobial activity and enhances storage stability. Further said specific class of isosorbide ether derivatives, namely those defined by formula (I) of the present invention boosts the activity of known preservatives.

Accordingly in a 1$^{st}$ aspect the present invention is directed to the use of an isosorbide ether derivative (IED) to improve storage stability of a composition, wherein said isosorbide ether derivative (IED) is of formula (I)

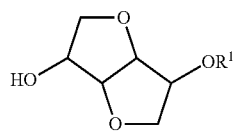

wherein
$R^1$ is a $C_8$ to $C_{12}$ n-alkyl residue or —$CH_2CH(OH)$—$R^2$, wherein $R^2$ is a $C_6$ to $C_{10}$ n-alkyl residue, preferably $R^1$ is —$(CH_2)_7CH_3$, —$(CH_2)_{11}CH_3$, —$CH_2CH(OH)$—$(CH_2)_7CH_3$ or —$CH_2CH(OH)$—$(CH_2)_9CH_3$.

According to a 2$^{nd}$ aspect the present invention is directed to the use of an isosorbide ether derivative (IED) as a preservative, preferably as an antimicrobial and/or fungicide, wherein said isosorbide ether derivative (IED) is of formula (I)

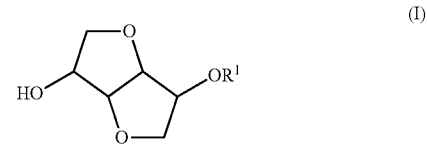

wherein
$R^1$ is a $C_8$ to $C_{12}$ n-alkyl residue or —$CH_2CH(OH)$—$R^2$, wherein $R^2$ is a $C_6$ to $C_{10}$ n-alkyl residue, preferably $R^1$ is —$(CH_2)_7CH_3$, —$(CH_2)_{11}CH_3$, —$CH_2CH(OH)$—$(CH_2)_7CH_3$ or —$CH_2CH(OH)$—$(CH_2)_9CH_3$.

In one preferred embodiment of the 2$^{nd}$ aspect of the present invention the isosorbide ether derivative (IED) has, preferably in a composition as defined herein, a minimum inhibitory concentration (MIC) of not more than 3000 ppm. Accordingly it is especially preferred that the isosorbide ether derivative (IED) according to the second aspect of the present invention has, preferably in a composition as defined herein, a minimum inhibitory concentration (MIC) for
  (a) gram positive bacteria of not more than 800 ppm; and/or
  (b) gram negative bacteria of not more than 2500 ppm; and/or
  (c) yeast and fungus of not more than 2500 ppm.

In one specific embodiment the isosorbide ether derivative (IED) according to the 2$^{nd}$ aspect of the present invention has, preferably in a composition as defined herein, a minimum inhibitory concentration (MIC) for *Candida albicans* of not more than 100 ppm. Further it is preferred that the isosorbide ether derivative (IED) according to the second aspect of the present invention is present in the composition in an amount of not more than 3000 ppm.

According to a 3$^{rd}$ embodiment the present invention is directed to the use of an isosorbide ether derivative (IED) as a preservative booster, i.e. to enhance the activity of a preservative (P), wherein said isosorbide ether derivative (IED) is of formula (I)

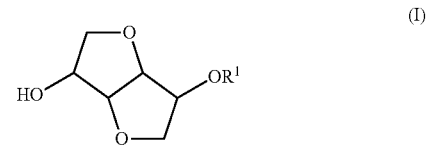

wherein
$R^1$ is a $C_8$ to $C_{12}$ n-alkyl residue or —$CH_2CH(OH)$—$R^2$, wherein $R^2$ is a $C_6$ to $C_{10}$ n-alkyl residue, preferably $R^1$ is —$(CH_2)_7CH_3$, —$(CH_2)_{11}CH_3$, —$CH_2CH(OH)$—$(CH_2)_7CH_3$ or —$CH_2CH(OH)$—$(CH_2)_9CH_3$.

Preferably the preservative (P) which activity is enhanced, i.e. boosted, is selected from the group consisting of formaldehyde, methylchloroisothiazolinone, methylisothiazolinone, benzoic acid including the salts thereof, benzoic acid ester derivatives, salicylic acid including the salts thereof, 4-hydroxy benzoic acid including the salts thereof, sorbic acid including the salts thereof, dehydroacetic acid including the salts thereof, dehydroacetic acid ester derivatives, phenoxyethanol, benzyl alcohol, 2-methylisothiazol-3(2H)-one, 4-isopropyl-m-cresol, and zinc pyrithione.

Preferably, the weight ratio between the preservative (P) and the isosorbide ether derivative (IDE) [(P)/(IDE)] is from 0.1/1 to 10/1.

Preferably said isosorbide ether derivative (IED) according to $1^{st}$, $2^{nd}$ and $3^{rd}$ aspect of the present invention is present in a composition, like a liquid composition. Still more preferably said isosorbide ether derivative (IED) according to $1^{st}$, $2^{nd}$ and $3^{rd}$ aspect of the present invention is present in a detergent or cosmetic composition.

In still another aspect ($4^{th}$ aspect), the present invention is directed to a composition comprising an isosorbide ether derivative of formula (I)

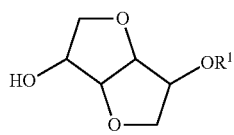

(I)

wherein
$R^1$ is a $C_8$ to $C_{12}$ n-alkyl residue or —$CH_2CH(OH)$—$R^2$, wherein $R^2$ is a $C_6$ to $C_{10}$ n-alkyl residue, preferably $R^1$ is —$(CH_2)_7CH_3$, —$(CH_2)_{11}CH_3$, —$CH_2CH(OH)$—$(CH_2)_7CH_3$ or —$CH_2CH(OH)$—$(CH_2)_9CH_3$, wherein further the amount of said isosorbide ether derivative in the composition does not exceed 3000 ppm.

Preferably said composition of the previous paragraph is a liquid composition and/or selected from the group consisting of detergent and cosmetic composition.

In the following the invention will be described in more detail.

The term "microorganism" is used to describe small organisms that are usually only visible using microscopic techniques. Microorganisms include all members of bacteria, archaea, protozoa, fungi, algae, and also certain animals, such as rotifers.

The term "preservative" is understood as known in the art. Accordingly a preservative is a compound which is added to a composition, like detergents or cosmetic compositions, to prevent growth (proliferation) of unwanted microorganisms such as pathogens and/or to prevent or slow degradation by microbial growth or by undesirable chemical changes of said composition. "Degradation" is especially understood as the process by which organic substances are broken down into simpler forms of matter.

The term "antimicrobial" according to this invention is/are (a) compound(s) that kills microorganisms or inhibits their growth. Preferably the relevant microorganisms are Gram negative bacteria, e.g. *Escherichia coli* and/or *Pseudomonas* spp (like *Pseudomonas aeruginosa*), or Gram positive bacteria, e.g. *Staphylococcus* spp (like *Staphylococcus aureus* and *Staphylococcus epidermis*), *Brevibacterium* spp (like *Brevibacterium epidermis*), *Propionibacterium* spp (like *Propionibacterium acnes*). A fungicide according to this invention is an antimicrobial compound that kills or inhibits growth of fungi or fungal spores (fungi includes yeasts). Preferably the relevant fungi are selected from the group consisting of *Aspergillus* spp (like *Aspergillus brasiliensis*), *Candida* spp (like *Candida albicans*) and *Malassezia* spp (like *Malassezia furfur*).

The term "composition" indicates that in addition to the isosorbide ether derivative (IED) according to this invention at least a further compound must be present. The additional compound(s) of a composition depend on the application of the composition and thus can vary in a broad range. "Cosmetic compositions" are to be understood herein as meaning all compositions known to the person skilled in the art which are exclusively or primarily intended to be used externally on the human body or in its oral cavity for cleaning, care, protection, maintaining a good condition, perfuming, changing the appearance or for the purposes of influencing body odor.

Accordingly the cosmetic composition according to the invention can be in particular a formulation for bodycare, e.g. a body milk, cream, lotion, sprayable emulsion, a product for eliminating body odor etc. It can be a surfactant-containing formulation such as e.g. foam bath and shower bath, hair shampoo and care rinse. Depending on the intended application, the cosmetic formulation can comprise a series of auxiliaries and additives, for example surfactants, oil bodies, emulsifiers, pearlescent waxes, consistency regulators, thickeners, superfatting agents, stabilizers, polymers, fats, waxes, lecithins, phospholipids, biogenic active ingredients, UV light protection factors, antioxidants, deodorants, antiperspirants, antidandruff agents, film formers, swelling agents, insect repellents, self-tanning agents, tyrosine inhibitors (depigmentation agents), hydrotropes, solubilizers, perfume oils, dyes etc.

Detergents typically contain surfactants preferably with cleaning properties in dilute solutions.

Use of the Isosorbide Ether Derivative According to this Invention as a Preservative One essential finding of the present invention is to use an isosorbide ether derivative (IED) as a preservative, wherein said isosorbide ether derivative (IED) is of formula (I)

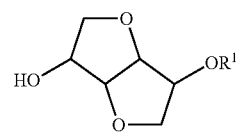

(I)

wherein
$R^1$ is a $C_8$ to $C_{12}$ n-alkyl residue or —$CH_2CH(OH)$—$R^2$, wherein $R^2$ is a $C_6$ to $C_{10}$ n-alkyl residue.

The term "n-alkyl" indicates that the residue is unbranched ("n") and does not contain any heteroatoms, i.e. contains only C and H atoms.

Accordingly if $R^1$ is a $C_6$ to $C_{12}$ n-alkyl residue, said residue is selected from the group consisting of —$(CH_2)_7CH_3$, —$(CH_2)_8CH_3$, —$(CH_2)_9CH_3$, —$(CH_2)_{10}CH_3$, and —$(CH_2)_{11}CH_3$, preferably selected from the group consisting of —$(CH_2)_7CH_3$, —$(CH_2)_9CH_3$, and —$(CH_2)_{11}CH_3$, more preferably selected from the group consisting of —$(CH_2)_7CH_3$, and —$(CH_2)_{11}CH_3$, still more preferably the $C_8$ to $C_{12}$ n-alkyl residue is —$(CH_2)_7CH_3$.

In case the $R^1$ is —$CH_2CH(OH)$—$R^2$, said residue $R^1$ is selected from the group consisting of —$CH_2CH(OH)$—$(CH_2)_5CH_3$, —$CH_2CH(OH)$—$(CH_2)_6CH_3$, —$CH_2CH(OH)$—$(CH_2)_7CH_3$, —$CH_2CH(OH)$—$(CH_2)_8CH_3$, and —$CH_2CH(OH)$—$(CH_2)_9CH_3$, preferably said residue $R^1$ is selected from the group consisting of —$CH_2CH(OH)$—$(CH_2)_5CH_3$, —$CH_2CH(OH)$—$(CH_2)_7CH_3$, —$CH_2CH$ (OH)—(CH$_2$)$_8$CH$_3$, and —CH$_2$CH(OH)—(CH$_2$)$_9$CH$_3$, more preferably said residue R$^1$ is selected from the group consisting of —CH$_2$CH(OH)—(CH$_2$)$_5$CH$_3$, —CH$_2$CH(OH)—(CH$_2$)$_7$CH$_3$, and —CH$_2$CH(OH)—(CH$_2$)$_9$CH$_3$, still more preferably said residue R$^1$ is —CH$_2$CH(OH)—(CH$_2$)$_7$CH$_3$ or —CH$_2$CH(OH)—(CH$_2$)$_9$CH$_3$, and yet more preferably said residue R$^1$ is —CH$_2$CH(OH)—(CH$_2$)$_9$CH$_3$.

In one specific preferred embodiment R$^1$ is selected from the group consisting of —(CH$_2$)$_7$CH$_3$, —(CH$_2$)$_{11}$CH$_3$, —CH$_2$CH(OH)—(CH$_2$)$_7$CH$_3$ and —CH$_2$CH(OH)—(CH$_2$)$_9$CH$_3$, preferably R$^1$ is —(CH$_2$)$_7$CH$_3$, or —CH$_2$CH(OH)—(CH$_2$)$_9$CH$_3$, more preferably R$^1$ is —(CH$_2$)$_7$CH$_3$.

As mentioned above the isosorbide ether derivative (IED) according to this invention is used as a preservative. Accordingly the isosorbide ether derivative (IED) is preferably part of a composition which contains in addition to the preservative "isosorbide ether derivative" (IED) at least a further compound which must be protected against degradation by microbial growth (including fungus growth), excessive proliferation of unwanted microorganisms or by undesirable chemical changes, preferably must be protected against degradation by microbial growth. The further compound(s) to be protected depend on the application of the composition and will be described in more detail below. It is especially preferred that the isosorbide ether derivative (IED) according to this invention is used as an antimicrobial, i.e. kills undesired microorganisms or inhibits their growth in the composition, and/or as a fungicide, i.e. kills or inhibits fungi or fungal spores. It is especially preferred that the isosorbide ether derivative (IED) is used in a composition as an antimicrobial against gram negative bacteria and/or gram positive bacteria, and/or as a fungicide against yeast and/or fungus, more preferably against Gram negative or Gram negative bacteria, yeast and/or fungus, still more preferably against Gram negative bacteria and/or fungus. In one specific embodiment the isosorbide ether derivative (IED) is used in a composition as an antimicrobial and/or as a fungicide against the group consisting of *Brevibacterium* spp (like *Brevibacterium epidermis*), *Propionibacterium* spp (like *Propionibacterium acnes*), *Staphylococcus* spp (like *Staphylococcus aureus* and/or *Staphylococcus epidermis*), *Escherichia coli*, *Pseudomonas* spp (like *Pseudomonas aeruginosa*), *Aspergillus* spp (like *Aspergillus brasiliensis*), *Candida* spp (like *Candida albicans*), and *Malassezia* spp (like *Malassezia furfur*), more preferably against the group consisting of *Brevibacterium epidermis, Propionibacterium acnes, Staphylococcus aureus, Staphylococcus epidermis, Escherichia coli, Pseudomonas aeruginosa, Aspergillus brasiliensis, Candida albicans*, and *Malassezia furfur*, still more preferably against the group consisting of *Brevibacterium epidermis, Propionibacterium acnes, Staphylococcus aureus, Staphylococcus epidermis, Aspergillus brasiliensis, Candida albicans*, and *Malassezia furfur* and yet more preferably against the group consisting of *Aspergillus brasiliensis, Candida albicans, Malassezia furfur* and yet more preferably against the group consisting of *Aspergillus brasiliensis, Candida albicans*, and *Malassezia furfur*.

Preferably the isosorbide ether derivative (IED) according to this invention used as a preservative, preferably used as an antimicrobial and/or as a fungicide, has a minimum inhibitory concentration (MIC) of not more than 3000 ppm, more preferably in the range of 1 to 3000 ppm, still more preferably in the range of 1 to 2500 ppm, yet more preferably in the range of 10 to 2500 ppm, like in the range of 10 to 2000 ppm or in the range of 10 to 1500 ppm. It is especially preferred that the minimum inhibitory concentration (MIC) given in the previous sentence is against gram negative bacteria, gram positive bacteria, yeast and/or fungus, more preferably against gram negative bacteria, yeast and/or fungus, still more preferably against the group consisting of *Brevibacterium* spp, *Propionibacterium* spp, *Staphylococcus* spp, *Escherichia coli, Pseudomonas* spp, *Aspergillus* spp, *Candida* spp, and *Malasse* spp, yet more preferably against the group consisting of *Brevibacterium epidermis, Propionibacterium acnes, Staphylococcus aureus, Staphylococcus epidermis, Escherichia coli, Pseudomonas aeruginosa, Aspergillus brasiliensis, Candida albicans*, and *Malassezia furfur*, still yet more preferably against the group consisting of *Brevibacterium epidermis, Propionibacterium acnes, Staphylococcus aureus, Staphylococcus epidermis, Aspergillus brasiliensis, Candida albicans*, and *Malassezia furfur*. Accordingly it is especially preferred that the isosorbide ether derivative (IED) is of formula (I) preferably with R$^1$ being selected from the group consisting of —(CH$_2$)$_7$CH$_3$, —(CH$_2$)$_{11}$CH$_3$, —CH$_2$CH(OH)—(CH$_2$)$_7$CH$_3$ and —CH$_2$CH(OH)—(CH$_2$)$_9$CH$_3$, more preferably R$^1$ is —(CH$_2$)$_7$CH$_3$, or —CH$_2$CH(OH)—(CH$_2$)$_9$CH$_3$, still more preferably R$^1$ is —(CH$_2$)$_7$CH$_3$.

Additionally or alternatively to the previous paragraph the isosorbide ether derivative (IED) according to this invention used as a preservative, preferably used as an antimicrobial, has a minimum inhibitory concentration (MIC) against gram positive bacteria, preferably against the group consisting of *Brevibacterium* spp, *Propionibacterium* spp and *Staphylococcus* sp, more preferably against the group consisting of *Brevibacterium epidermis, Propionibacterium acnes, Staphylococcus aureus*, and *Staphylococcus epidermis*, of not more than 1000 ppm, like of not more than 800 ppm, more preferably in the range of 1 to 1000 ppm, still more preferably in the range of 5 to 800 ppm, yet more preferably in the range of 20 to 700 ppm, like in the range of 50 to 600 ppm. Accordingly it is especially preferred that the isosorbide ether derivative (IED) is of formula (I) preferably with R$^1$ being selected from the group consisting of —(CH$_2$)$_7$CH$_3$, —(CH$_2$)$_{11}$CH$_3$, —CH$_2$CH(OH)—(CH$_2$)$_7$CH$_3$ and —CH$_2$CH(OH)—(CH$_2$)$_9$CH$_3$, more preferably R$^1$ is —(CH$_2$)$_{11}$CH$_3$, or —CH$_2$CH(OH)—(CH$_2$)$_7$CH$_3$, still more preferably R$^1$ is —(CH$_2$)$_{11}$CH$_3$.

Preferably the isosorbide ether derivative (IED) according to this invention used as a preservative, preferably used as an antimicrobial, has a minimum inhibitory concentration (MIC) against gram negative bacteria, preferably against *Escherichia coli* and *Pseudomonas* spp, more preferably against *Escherichia coli* and *Pseudomonas aeruginosa*, of not more than 3000 ppm, like not more than 2500 ppm, more preferably in the range of 10 to 3000 ppm, still more preferably in the range of 100 to 2500 ppm, yet more preferably in the range of 500 to 2500 ppm. Accordingly it is especially preferred that the isosorbide ether derivative (IED) is of formula (I) preferably with R$^1$ being —(CH$_2$)$_7$CH$_3$ or —CH$_2$CH(OH)—(CH$_2$)$_9$CH$_3$, more preferably R$^1$ is —(CH$_2$)$_7$CH$_3$.

In another embodiment the isosorbide ether derivative according to this invention used as a preservative, preferably used as a fungicide, has a minimum inhibitory concentration (MIC) against yeast and/or fungus, preferably against the group consisting of *Aspergillus* spp, *Candida* spp, and *Malasse* spp, more preferably against the group consisting of *Aspergillus brasiliensis, Candida albicans*, and *Malassezia furfur*, of not more than 3000 ppm, like of not more than 2500, more preferably in the range of 1 to 3000 ppm, still more preferably in the range of 1 to 2500 ppm, yet more preferably in the range of 1 to 2000 ppm, like in the range of 10 to 1500 ppm. Accordingly it is especially preferred that the isosorbide ether derivative (IED) is of formula (I) preferably with $R^1$ being selected from the group consisting of —CH$_2$CH(OH)—(CH$_2$)$_6$CH$_3$, —CH$_2$CH(OH)—(CH$_2$)$_7$CH$_3$, —CH$_2$CH(OH)—(CH$_2$)$_8$CH$_3$, and —CH$_2$CH(OH)—(CH$_2$)$_9$CH$_3$, more preferably selected from the group consisting of —(CH$_2$)$_7$CH$_3$, —(CH$_2$)$_{11}$CH$_3$, and —CH$_2$CH(OH)—(CH$_2$)$_9$CH$_3$, still more preferably $R^1$ is —(CH$_2$)$_{11}$CH$_3$, or —CH$_2$CH(OH)—(CH$_2$)$_9$CH$_3$, still yet more preferably $R^1$ is —CH$_2$CH(OH)—(CH$_2$)$_9$CH$_3$.

It is especially preferred that the isosorbide ether derivative (IED) according to this invention used as a preservative, preferably used as a fungicide, has a minimum inhibitory concentration (MIC) against fungus, more preferably against *Aspergillus* spp and *Candida* spp, yet more preferably against *Aspergillus brasiliensis* and *Candida albicans* of not more than 1000 ppm, more preferably in the range of 1 to 1000 ppm, still more preferably in the range of 1 to 500 ppm, yet more preferably in the range of 1 to 100 ppm, like in the range of 1 to 60 ppm. Accordingly it is especially preferred that the isosorbide ether derivative (IED) is of formula (I) preferably with $R^1$ being selected from the group consisting of —CH$_2$CH(OH)—(CH$_2$)$_6$CH$_3$, —CH$_2$CH(OH)—(CH$_2$)$_7$CH$_3$, —CH$_2$CH(OH)—(CH$_2$)$_8$CH$_3$, and —CH$_2$CH(OH)—(CH$_2$)$_9$CH$_3$, more preferably selected from the group consisting of —(CH$_2$)$_7$CH$_3$, —(CH$_2$)$_{11}$CH$_3$, and —CH$_2$CH(OH)—(CH$_2$)$_9$CH$_3$, still more preferably $R^1$ is —(CH$_2$)$_{11}$CH$_3$, or —CH$_2$CH(OH)—(CH$_2$)$_9$CH$_3$, still yet more preferably $R^1$ is —(CH$_2$)$_{11}$CH$_3$.

In one preferred embodiment the isosorbide ether derivative (IED) according to this invention used as a preservative, preferably used as a fungicide, has a minimum inhibitory concentration (MIC) against *Candida* spp, more preferably against *Candida albicans*, of not more than 100 ppm, more preferably in the range of 1 to 100 ppm, still more preferably in the range of 1 to 80 ppm, yet more preferably in the range of 1 to 60 ppm. Accordingly it is especially preferred that the isosorbide ether derivative (IED) is of formula (I) preferably with $R^1$ being selected from the group consisting of —CH$_2$CH(OH)—(CH$_2$)$_6$CH$_3$, —CH$_2$CH(OH)—(CH$_2$)$_7$CH$_3$, —CH$_2$CH(OH)—(CH$_2$)$_8$CH$_3$, and —CH$_2$CH(OH)—(CH$_2$)$_9$CH$_3$, more preferably selected from the group consisting of —(CH$_2$)$_7$CH$_3$, —(CH$_2$)$_{11}$CH$_3$, and —CH$_2$CH(OH)—(CH$_2$)$_9$CH$_3$, still more preferably $R^1$ is —(CH$_2$)$_{11}$CH$_3$, or —CH$_2$CH(OH)—(CH$_2$)$_9$CH$_3$, yet more preferably $R^1$ is —(CH$_2$)$_{11}$CH$_3$.

Preferably the isosorbide ether derivative (IED) according to this invention is part of a composition, preferably a liquid composition, like an aqueous composition. It is preferred that the amount of the isosorbide ether derivative (IED) in total is not more than 3000 ppm, preferably in the range of 10 to 3000 ppm, more preferably in the range of 10 to 2500 ppm.

Accordingly in the composition different isosorbide ether derivatives (IED) according to this invention might be used as long as the total amount as indicated in this paragraph is not exceeded. In one preferred embodiment just one isosorbide ether derivatives (IED) according to this invention is present in the composition. This information is applicable for all embodiments defined herein, especially for the additional uses and compositions defined below.

Further it might be possible that isosorbide ether (IE) or by-products (BP) not belonging to formula (I) might be present. However it is preferred that those compounds, namely isosorbide ether (IE) or by-products (BP) not belonging to formula (I), are present in minor amounts. Minor amounts according to this invention means that the amount is not more than 25 wt.-%, still more preferably not more than 15 wt.-%, yet more preferably not more than 10 wt.-%, still yet more preferably not more than 5.0 wt.-%, like not more than 3.0 wt.-%, e.g. not more than 2.0 wt.-% based on the total amounts of isosorbide ether derivatives, i.e. total amount of IED, BP and IE. This information is applicable for all embodiments defined herein, especially for the additional uses and compositions defined below.

The additional component(s) present in the composition in which the isosorbide ether derivative (IED) is used as a preservative depends on the end applications of the composition. Accordingly in a preferred embodiment the composition in which the isosorbide ether derivative (IED) is used is selected from the group consisting of detergent and cosmetic composition. Preferably the composition, e.g. the detergent or the cosmetic composition, is a liquid composition, like an aqueous composition.

The detergent according to this invention can be in form of a liquid, a gel or a solid. Preferably the detergents according to this invention are liquid. Preferably the detergent contains in addition to the isosorbide ether derivative (IED) as defined herein surfactants preferably with cleaning properties in dilute solutions. Preferably the surfactant can be nonionic or amphoteric. The fraction of surfactants may about 1 to 30 wt.-%, preferably 5 to 25 wt.-% and in particular 10 to 20 wt.-%. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides and glucuronic acid derivatives, fatty acid N-alkylglucamides, protein hydrolyzates (in particular wheat-based vegetable products), polyol fatty acid esters, sugar esters, sorbitan esters, polysorbates and amine oxides. If the nonionic surfactants contain polyglycol ether chains, these can have a conventional homolog distribution, but preferably have a narrowed homolog distribution. Typical examples of amphoteric surfactants are alkylbetaines, alkylamidobetaines, aminopropionates, aminoglycinates, imidazoliniumbetaines and sulfobetaines. Said surfactants are exclusively known compounds.

Further optional ingredients may be but are not limited to viscosity modifiers, cationic surfactants, foam boosting or foam reducing agents, perfumes, dyes, optical brighteners, dye transfer inhibiting agents and other preservatives to those discussed herein. In this regard it needs to be mentioned that the isosorbide ether derivative in the amounts as discussed above present in the detergents cannot act as a foam reducing agent or emollient.

Cosmetic compositions according to this invention are exclusively or primarily intended to be used externally on the human body or in its oral cavity for cleaning, care, protection, maintaining a good condition, perfuming, changing the appearance or for the purposes of influencing body odor.

Preferably the cosmetic composition contains in addition to the isosorbide ether derivative (IED) as defined herein surfactants. Surfactants which may be present are anionic, nonionic, cationic and/or amphoteric or zwitterionic surfactants. In surfactant-containing cosmetic preparations, for example shower gels, foam baths, shampoos etc., preferably at least one anionic surfactant is present. The fraction of surfactants is preferably about 1 to 30, preferably 5 to 25 and in particular 10 to 20% by weight.

Typical examples of anionic surfactants are soaps, alkylbenzenesulfonates, alkanesulfonates, olefinsulfonates, alkyl ether sulfonates, glycerol ether sulfonates, α-methyl ester sulfonates, sulfo fatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglycoside sulfates, protein fatty acid condensates (in particular wheat-based vegetable products) and alkyl (ether) phosphates. If the anionic surfactants contain polyglycol ether chains, these can have a conventional homolog distribution, but preferably have a narrowed homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides and glucuronic acid derivatives, fatty acid N-alkylglucamides, protein hydrolyzates (in particular wheat-based vegetable products), polyol fatty acid esters, sugar esters, sorbitan esters, polysorbates and amine oxides. If the nonionic surfactants contain polyglycol ether chains, these can have a conventional homolog distribution, but preferably have a narrowed homolog distribution. Typical examples of cationic surfactants are quaternary ammonium compounds, such as, for example, dimethyldistearylammonium chloride, and ester quats, in particular quaternized fatty acid trialkanolamine ester salts. Typical examples of amphoteric or zwitterionic surfactants are alkylbetaines, alkylamidobetaines, aminopropionates, aminoglycinates, imidazoliniumbetaines and sulfobetaines. Typical examples of particularly suitable mild, i.e. particularly skin-compatible, surfacatants are fatty alcohol polyglycol ether sulfates, monoglyceride sulfates, mono- and/or dialkyl sulfosuccinates, fatty acid isethionates, fatty acid sarcosinates, fatty acid taurides, fatty acid glutamates, α-olefinsulfonates, ether carboxylic acids, alkyl oligoglucosides, fatty acid glucamides, alkylamidobetaines, amphoacetals and/or protein fatty acid condensates, the latter preferably based on wheat proteins.

In another embodiment, the amount of the isosorbide ether derivative (IED) might be above the indicated upper limit of 3000 ppm in a composition. In such cases the isosorbide ether derivative (IED) shall not only be used as a preservative, preferably as an antimicrobial and/or as a fungicide, but also as a thickener and/or emulsifier, and/or foam booster and/or sensory modifier and/or consistency factor and/or emollient. Accordingly in another embodiment the present invention is directed to the use of the isosorbide ether derivative (IED) in a composition as (a) a preservative, preferably an antimicrobial and/or as a fungicide, more preferably an antimicrobial and/or as a fungicide against gram negative bacteria, gram positive bacteria, yeast and/or fungus, more preferably against gram negative bacteria, yeast and/or fungus, still more preferably against the group consisting of *Brevibacterium* spp, *Propionibacterium* spp, *Staphylococcus* spp, *Escherichia coli*, *Pseudomonas* spp, *Aspergillus* spp, *Candida* spp, and *Malasse* spp, yet more preferably against the group consisting of *Brevibacterium epidermis*, *Propionibacterium acnes*, *Staphylococcus aureus*, *Staphylococcus epidermis*, *Escherichia coli*, *Pseudomonas aeruginosa*, *Aspergillus brasiliensis*, *Candida albicans*, and *Malassezia furfur*, still yet more preferably against the group consisting of *Brevibacterium epidermis*, *Propionibacterium acnes*, *Staphylococcus aureus*, *Staphylococcus epidermis*, *Aspergillus brasiliensis*, *Candida albicans*, and *Malassezia furfur*, and (b) thickener and/or emulsifier, and/or foam booster and/or sensory modifier and/or consistency factor and/or emollient, more preferably as thickener and/or emulsifier, said isosorbide ether derivative (IED) is of formula (I)

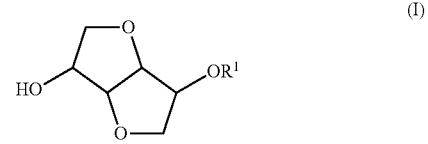

(I)

wherein
$R^1$ is a $C_8$ to $C_{12}$ n-alkyl residue or —$CH_2CH(OH)$—$R^2$, wherein $R^2$ is a $C_6$ to $C_{10}$ n-alkyl residue, preferably with $R^1$ being selected from the group consisting of —$CH_2CH(OH)$—$(CH_2)_6CH_3$, —$CH_2CH(OH)$—$(CH_2)_7CH_3$, —$CH_2CH(OH)$—$(CH_2)_8CH_3$, and —$CH_2CH(OH)$—$(CH_2)_9CH_3$,
with the proviso that the total amount of isosorbide ether derivative (IED) according to formula (I) is above 3000 ppm, preferably equal or above 3010 ppm, more preferably in the range of above 3000 to 50000 ppm, yet more preferably in the range of equal or above 3010 ppm to 5000 ppm, still more preferably in the range of 5000 to 40000 ppm.

In such a case the composition is preferably a detergent or a cosmetic composition. More preferably the composition, e.g. the detergent or the cosmetic composition, is a liquid composition, like an aqueous composition.

Use of the Isosorbide Ether Derivative According to this Invention as a Preservative Booster One further finding of the present invention is to use the isosorbide ether derivative (IED) as a preservative booster, wherein said isosorbide ether derivative (IED) is of formula (I)

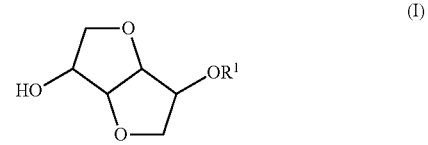

(I)

wherein
$R^1$ is a $C_8$ to $C_{12}$ n-alkyl residue or —$CH_2CH(OH)$—$R^2$, wherein $R^2$ is a $C_6$ to $C_{10}$ n-alkyl residue.

The term "n-alkyl" indicates that the residue is unbranched ("n") and does not contain any heteroatoms, i.e. contains only C and H atoms.

Accordingly if $R^1$ is a $C_6$ to $C_{12}$ n-alkyl residue, said residue is selected from the group consisting of —$(CH_2)_7CH_3$, —$(CH_2)_8CH_3$, —$(CH_2)_9CH_3$, —$(CH_2)_{10}CH_3$, and —$(CH_2)_{11}CH_3$, preferably selected from the group consisting of —$(CH_2)_7CH_3$, —$(CH_2)_9CH_3$, and —$(CH_2)_{11}CH_3$, more preferably selected from the group consisting of —$(CH_2)_7CH_3$, and —$(CH_2)_{11}CH_3$, still more preferably the $C_8$ to $C_{12}$ n-alkyl residue is —$(CH_2)_7CH_3$.

In case the $R^1$ is —$CH_2CH(OH)$—$R^2$, said residue $R^1$ is selected from the group consisting of —$CH_2CH(OH)$—$(CH_2)_5CH_3$, —$CH_2CH(OH)$—$(CH_2)_6CH_3$, —$CH_2CH(OH)$—$(CH_2)_7CH_3$, —$CH_2CH(OH)$—$(CH_2)_8CH_3$, and —CH₂CH(OH)—(CH₂)₉CH₃, preferably said residue R¹ is selected from the group consisting of —CH₂CH(OH)—(CH₂)₅CH₃, —CH₂CH(OH)—(CH₂)₇CH₃, —CH₂CH(OH)—(CH₂)₈CH₃, and —CH₂CH(OH)—(CH₂)₉CH₃, more preferably said residue R¹ is selected from the group consisting of —CH₂CH(OH)—(CH₂)₅CH₃, —CH₂CH(OH)—(CH₂)₇CH₃, and —CH₂CH(OH)—(CH₂)₉CH₃, still more preferably said residue R¹ is —CH₂CH(OH)—(CH₂)₇CH₃ or —CH₂CH(OH)—(CH₂)₉CH₃, and yet more preferably said residue R¹ is —CH₂CH(OH)—(CH₂)₉CH₃.

In one specific preferred embodiment R¹ is selected from the group consisting of —(CH₂)₇CH₃, —(CH₂)₁₁CH₃, —CH₂CH(OH)—(CH₂)₇CH₃ and —CH₂CH(OH)—(CH₂)₉CH₃.

A "preservative booster" according to this invention means a substance which increases or enhances the activity of a preservative (P). That is the activity of a preservative (P) in a composition is increased due to the presence of the preservative booster. This increased activity is especially observed for a preservative selected from the group consisting of formaldehyde, methylchloroisothiazolinone, methylisothiazolinone, benzoic acid including the salts thereof, benzoic acid ester derivatives, salicylic acid including the salts thereof, 4-hydroxy benzoic acid including the salts thereof, sorbic acid including the salts thereof, dehydroacetic acid including the salts thereof, dehydroacetic acid ester derivatives, phenoxyethanol, benzyl alcohol, 2-methylisothiazol-3(2H)-one, 4-isopropyl-m-cresol, and zinc pyrithione, more preferably selected from a group consisting of formaldehyde, methylchloroisothiazolinone, methylisothiazolinone, benzoic acid including the salts thereof, benzoic acid ester derivatives, salicylic acid including the salts thereof, 4-hydroxy benzoic acid including the salts thereof, dehydroacetic acid including the salts thereof, dehydroacetic acid ester derivatives, phenoxyethanol, benzyl alcohol, 2-methylisothiazol-3(2H)-one, 4-isopropyl-m-cresol, and zinc pyrithione.

Preferably, the weight ratio between the preservative (P) and the isosorbide ether derivative (IDE) [(P)/(IDE)] is from 0.1/1 to 10/1, more preferably from 1/1 to 8/1.

Typically the total amount of the isosorbide ether derivative (IED) according to formula (I) if used as a preservative booster is in the range of 10 to 5000 ppm based on the total amount of the composition. In one embodiment of the invention the amount of the isosorbide ether derivative (IED) according to formula (I) if used as a preservative booster is not more than 3000 ppm, preferably in the range of 10 to 3000 ppm, more preferably in the range of 10 to 2500 ppm, based on the total amount of the composition. In another embodiment of the invention the amount of the isosorbide ether derivative (IED) according to formula (I) if used as a preservative booster is above 3000 ppm, preferably equal or above 3010 ppm, more preferably in the range of above 3000 to 50000 ppm, yet more preferably in the range of equal or above 3010 ppm to 5000 ppm, still more preferably in the range of 5000 to 40000 ppm. The latter embodiment is especially applicable in case the isosorbide ether derivative (IED) is not only used as preservative booster but also in addition as a thickener and/or emulsifier, and/or foam booster and/or sensory modifier and/or consistency factor and/or emollient, more preferably as thickener and/or emulsifier.

Preferably the isosorbide ether derivative (IED) if used as a preservative booster is part of a composition, preferably a liquid composition, like an aqueous composition. Preferably the composition in which the isosorbide ether derivative (IED) is used is selected from the group consisting of detergent and cosmetic composition. Preferably the composition, e.g. the detergent or the cosmetic composition, is a liquid composition, like an aqueous composition. Concerning preferred embodiments of a detergent or cosmetic composition reference is made to the information provided above.

Use of the Isosorbide Ether Derivative According to this Invention as a Storage Stabilizer One further finding of the present invention is to use the isosorbide ether derivative (IED) as a storage stabilizer, i.e. to improve storage stability, wherein said isosorbide ether derivative (IED) is of formula (I)

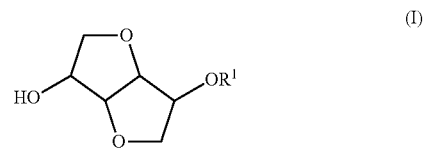

wherein
R¹ is a C₈ to C₁₂ n-alkyl residue or —CH₂CH(OH)—R², wherein R² is a C₆ to C₁₀ n-alkyl residue.

The term "n-alkyl" indicates that the residue is unbranched ("n") and does not contain any heteroatoms, i.e. contains only C and H atoms.

Accordingly if R¹ is a C₆ to C₁₂ n-alkyl residue, said residue is selected from the group consisting of —(CH₂)₇CH₃, —(CH₂)₈CH₃, —(CH₂)₉CH₃, —(CH₂)₁₀CH₃, and —(CH₂)₁₁CH₃, preferably selected from the group consisting of —(CH₂)₇CH₃, —(CH₂)₉CH₃, and —(CH₂)₁₁CH₃, more preferably selected from the group consisting of —(CH₂)₇CH₃, and —(CH₂)₁₁CH₃, still more preferably the C₈ to C₁₂ n-alkyl residue is —(CH₂)₇CH₃.

In case the R¹ is —CH₂CH(OH)—R², said residue R¹ is selected from the group consisting of —CH₂CH(OH)—(CH₂)₅CH₃, —CH₂CH(OH)—(CH₂)₆CH₃, —CH₂CH(OH)—(CH₂)₇CH₃, —CH₂CH(OH)—(CH₂)₈CH₃, and —CH₂CH(OH)—(CH₂)₉CH₃, preferably said residue R¹ is selected from the group consisting of —CH₂CH(OH)—(CH₂)₅CH₃, —CH₂CH(OH)—(CH₂)₇CH₃, —CH₂CH(OH)—(CH₂)₈CH₃, and —CH₂CH(OH)—(CH₂)₉CH₃, more preferably said residue R¹ is selected from the group consisting of —CH₂CH(OH)—(CH₂)₅CH₃, —CH₂CH(OH)—(CH₂)₇CH₃, and —CH₂CH(OH)—(CH₂)₉CH₃, still more preferably said residue R¹ is —CH₂CH(OH)—(CH₂)₇CH₃ or —CH₂CH(OH)—(CH₂)₉CH₃, and yet more preferably said residue R¹ is —CH₂CH(OH)—(CH₂)₉CH₃.

In one specific preferred embodiment R¹ is selected from the group consisting of —(CH₂)₇CH₃, —(CH₂)₁₁CH₃, —CH₂CH(OH)—(CH₂)₇CH₃ and —CH₂CH(OH)—(CH₂)₉CH₃.

A "storage stabilizer" according to this invention means a substance which increases the life time of a composition. That is the components of the composition, especially the components making up the essential part of the composition, are not degraded at all or the degradation process is retarded or attenuated, preferably the degradation process is retarded.

Typically the total amount of the isosorbide ether derivative (IED) according to formula (I) if used as a storage stabilizer is in the range of 10 to 5000 ppm based on the total amount of the composition. In one embodiment of the invention the amount of the isosorbide ether derivative (IED) according to formula (I) if used as a storage stabilizer is not more than 3000 ppm, preferably in the range of 10 to 3000 ppm, more preferably in the range of 10 to 2500 ppm, based on the total amount of the composition. In another embodiment of the invention the amount of the isosorbide ether derivative (IED) according to formula (I) if used as a storage stabilizer is above 3000 ppm, preferably equal or above 3010 ppm, more preferably in the range of above 3000 to 50000 ppm, yet more preferably in the range of equal or above 3010 ppm to 5000 ppm, still more preferably in the range of 5000 to 40000 ppm. The latter embodiment is especially applicable in case the isosorbide ether derivative (IED) is not only used as storage stabilizer but also in addition as a thickener and/or emulsifier, and/or foam booster and/or sensory modifier and/or consistency factor and/or emollient, more preferably as thickener and/or emulsifier.

Preferably the isosorbide ether derivative (IED) if used as storage stabilizer is part of a composition, preferably a liquid composition, like an aqueous composition. Preferably the composition in which the isosorbide ether derivative (IED) is used is selected from the group consisting of detergent and cosmetic composition. Preferably the composition, e.g. the detergent or the cosmetic composition, is a liquid composition, like an aqueous composition. Concerning preferred embodiments of a detergent or cosmetic composition reference is made to the information provided above.

Composition Comprising Isosorbide Ether Derivative(s) of Formula (I) in an Amount Not Exceeding 3000 ppm The invention is additionally directed to a composition comprising an isosorbide ether derivative (IED) of formula (I)

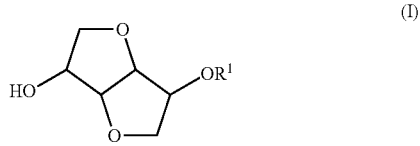

(I)

wherein
R$^1$ is a C$_8$ to C$_{12}$ n-alkyl residue or —CH$_2$CH(OH)—R$^2$, wherein R$^2$ is a C$_6$ to C$_{10}$ n-alkyl residue wherein further the amount of said isosorbide ether derivative (IED) in the composition does not exceed 3000 ppm.

The term "n-alkyl" indicates that the residue is unbranched ("n") and does not contain any heteroatoms, i.e. contains only C and H atoms.

Accordingly if R$^1$ is a C$_6$ to C$_{12}$ n-alkyl residue, said residue is selected from the group consisting of —(CH$_2$)$_7$CH$_3$, —(CH$_2$)$_8$CH$_3$, —(CH$_2$)$_9$CH$_3$, —(CH$_2$)$_{10}$CH$_3$, and —(CH$_2$)$_{11}$CH$_3$, preferably selected from the group consisting of —(CH$_2$)$_7$CH$_3$, —(CH$_2$)$_9$CH$_3$, and —(CH$_2$)$_{11}$CH$_3$, more preferably selected from the group consisting of —(CH$_2$)$_7$CH$_3$, and —(CH$_2$)$_{11}$CH$_3$, still more preferably the C$_8$ to C$_{12}$ n-alkyl residue is —(CH$_2$)$_7$CH$_3$.

In case the R$^1$ is —CH$_2$CH(OH)—R$^2$, said residue R$^1$ is selected from the group consisting of —CH$_2$CH(OH)—(CH$_2$)$_5$CH$_3$, —CH$_2$CH(OH)—(CH$_2$)$_6$CH$_3$, —CH$_2$CH(OH)—(CH$_2$)$_7$CH$_3$, —CH$_2$CH(OH)—(CH$_2$)$_8$CH$_3$, and —CH$_2$CH(OH)—(CH$_2$)$_9$CH$_3$, preferably said residue R$^1$ is selected from the group consisting of —CH$_2$CH(OH)—(CH$_2$)$_5$CH$_3$, —CH$_2$CH(OH)—(CH$_2$)$_7$CH$_3$, —CH$_2$CH(OH)—(CH$_2$)$_8$CH$_3$, and —CH$_2$CH(OH)—(CH$_2$)$_9$CH$_3$, more preferably said residue R$^1$ is selected from the group consisting of —CH$_2$CH(OH)—(CH$_2$)$_5$CH$_3$, —CH$_2$CH(OH)—(CH$_2$)$_7$CH$_3$, and —CH$_2$CH(OH)—(CH$_2$)$_9$CH$_3$, still more preferably said residue R$^1$ is —CH$_2$CH(OH)—(CH$_2$)$_7$CH$_3$ or —CH$_2$CH(OH)—(CH$_2$)$_9$CH$_3$, and yet more preferably said residue R$^1$ is —CH$_2$CH(OH)—(CH$_2$)$_9$CH$_3$.

In one specific preferred embodiment R$^1$ is selected from the group consisting of —(CH$_2$)$_7$CH$_3$, —(CH$_2$)$_{11}$CH$_3$, —CH$_2$CH(OH)—(CH$_2$)$_7$CH$_3$ and —CH$_2$CH(OH)—(CH$_2$)$_9$CH$_3$, preferably R$^1$ is —(CH$_2$)$_7$CH$_3$, or —CH$_2$CH(OH)—(CH$_2$)$_9$CH$_3$, more preferably R$^1$ is —(CH$_2$)$_7$CH$_3$.

Preferably the composition is a detergent or a cosmetic composition.

The total amount of isosorbide ether derivative (IED) in the composition is not more than 3000 ppm, preferably in the range of 10 to 3000 ppm, more preferably in the range of 10 to 2500 ppm, based on the total amount of the composition. Accordingly in the composition different isosorbide ether derivatives (IED) of formula (I) according to this invention might be used as long as the total amount as indicated in this paragraph is not exceeded. However it is preferred that just one isosorbide ether derivative (IED) of formula (I) is present in the composition.

Further it might be possible that isosorbide ether (IE) or by-products (BP) not belonging to formula (I) might be present. However it is preferred that those compounds, namely isosorbide ether (IE) and by-products (BP) not belonging to formula (I), are present in minor amounts. Minor amounts according to this invention means that the amount is not more than 25 wt.-%, still more preferably not more than 15 wt.-%, yet more preferably not more than 10 wt.-%, still yet more preferably not more than 5.0 wt.-%, like not more than 3.0 wt.-%, e.g. not more than 2.0 wt.-% based on the total amounts of isosorbide ether derivatives, i.e. total amount of IED, BP and IE.

In a preferred embodiment the composition is a detergent or a cosmetic composition. Preferably the composition, e.g. the detergent or the cosmetic composition, is a liquid composition, like an aqueous composition.

Preferably the composition may comprise in addition to the isosorbide ether derivative (IED) of formula (I) according to this invention at least one, preferably one, preservative (P) selected from the group consisting of formaldehyde, methylchloroisothiazolinone, methylisothiazolinone, benzoic acid including the salts thereof, benzoic acid ester derivatives, salicylic acid including the salts thereof, 4-hydroxy benzoic acid including the salts thereof, sorbic acid including the salts thereof, dehydroacetic acid including the salts thereof, dehydroacetic acid ester derivatives, phenoxyethanol, benzyl alcohol, 2-methylisothiazol-3(2H)-one, 4-isopropyl-m-cresol, and zinc pyrithione, more preferably selected from a group consisting of formaldehyde, methylchloroisothiazolinone, methylisothiazolinone, benzoic acid including the salts thereof, benzoic acid ester derivatives, salicylic acid including the salts thereof, 4-hydroxy benzoic acid including the salts thereof, dehydroacetic acid including the salts thereof, dehydroacetic acid ester derivatives, phenoxyethanol, benzyl alcohol, 2-methylisothiazol-3(2H)-one, 4-isopropyl-m-cresol, and zinc pyrithione.

In case the composition comprises additionally at least one preservative (P), the weight ratio between said preservative(s) (P) and the isosorbide ether derivative(s) (IDE) [(P)/(IDE)] is from 0.1/1 to 10/1, more preferably from 1/1 to 8/1.

Concerning definitions and further preferred embodiments, reference is made to the information under the heading "Use of the isosorbide ether derivative according to this invention as a preservative" or "Use of the isosorbide ether derivative according to this invention as a preservative booster".

Composition Comprising Isosorbide Ether Derivative(s) of Formula (I) and at Least One Preservative (P)

The invention is additionally directed to a composition comprising (a) an isosorbide ether derivative (IDE) of formula (I)

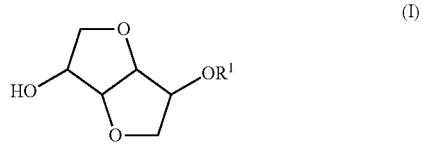

(I)

wherein
R$^1$ is a C$_8$ to C$_{12}$ n-alkyl residue or —CH$_2$CH(OH)—R$^2$, wherein R$^2$ is a C$_6$ to C$_{10}$ n-alkyl residue, and (b) a preservative (P) selected from the group consisting of formaldehyde, methylchloroisothiazolinone, methylisothiazolinone, benzoic acid including the salts thereof, benzoic acid ester derivatives, salicylic acid including the salts thereof, 4-hydroxy benzoic acid including the salts thereof, sorbic acid including the salts thereof, dehydroacetic acid including the salts thereof, dehydroacetic acid ester derivatives, phenoxyethanol, benzyl alcohol, 2-methylisothiazol-3(2H)-one, 4-isopropyl-m-cresol, and zinc pyrithione, more preferably selected from a group consisting of formaldehyde, methylchloroisothiazolinone, methylisothiazolinone, benzoic acid including the salts thereof, benzoic acid ester derivatives, salicylic acid including the salts thereof, 4-hydroxy benzoic acid including the salts thereof, dehydroacetic acid including the salts thereof, dehydroacetic acid ester derivatives, phenoxyethanol, benzyl alcohol, 2-methylisothiazol-3(2H)-one, 4-isopropyl-m-cresol, and zinc pyrithione, wherein the weight ratio between the preservative (P) and the isosorbide ether derivative (IDE) [(P)/(IDE)] is from 0.1/1 to 10/1.

The term "n-alkyl" indicates that the residue is unbranched ("n") and does not contain any heteroatoms, i.e. contains only C and H atoms.

Accordingly if R$^1$ is a C$_6$ to C$_{12}$ n-alkyl residue, said residue is selected from the group consisting of —(CH$_2$)$_7$CH$_3$, —(CH$_2$)$_8$CH$_3$, —(CH$_2$)$_9$CH$_3$, —(CH$_2$)$_{10}$CH$_3$, and —(CH$_2$)$_{11}$CH$_3$, preferably selected from the group consisting of —(CH$_2$)$_7$CH$_3$, —(CH$_2$)$_9$CH$_3$, and —(CH$_2$)$_{11}$CH$_3$, more preferably selected from the group consisting of —(CH$_2$)$_7$CH$_3$, and —(CH$_2$)$_{11}$CH$_3$, still more preferably the C$_8$ to C$_{12}$ n-alkyl residue is —(CH$_2$)$_7$CH$_3$.

In case the R$^1$ is —CH$_2$CH(OH)—R$^2$, said residue R$^1$ is selected from the group consisting of —CH$_2$CH(OH)—(CH$_2$)$_5$CH$_3$, —CH$_2$CH(OH)—(CH$_2$)$_6$CH$_3$, —CH$_2$CH(OH)—(CH$_2$)$_7$CH$_3$, —CH$_2$CH(OH)—(CH$_2$)$_9$CH$_3$, and —CH$_2$CH(OH)—(CH$_2$)$_9$CH$_3$, preferably said residue R$^1$ is selected from the group consisting of —CH$_2$CH(OH)—(CH$_2$)$_5$CH$_3$, —CH$_2$CH(OH)—(CH$_2$)$_7$CH$_3$, —CH$_2$CH(OH)—(CH$_2$)$_9$CH$_3$, and —CH$_2$CH(OH)—(CH$_2$)$_9$CH$_3$, more preferably said residue R$^1$ is selected from the group consisting of —CH$_2$CH(OH)—(CH$_2$)$_5$CH$_3$, —CH$_2$CH(OH)—(CH$_2$)$_7$CH$_3$, and —CH$_2$CH(OH)—(CH$_2$)$_9$CH$_3$, still more preferably said residue R$^1$ is —CH$_2$CH(OH)—(CH$_2$)$_7$CH$_3$ or —CH$_2$CH(OH)—(CH$_2$)$_9$CH$_3$, and yet more preferably said residue R$^1$ is —CH$_2$CH(OH)—(CH$_2$)$_9$CH$_3$.

In one specific preferred embodiment R$^1$ is selected from the group consisting of —(CH$_2$)$_7$CH$_3$, —(CH$_2$)$_{11}$CH$_3$, —CH$_2$CH(OH)—(CH$_2$)$_7$CH$_3$ and —CH$_2$CH(OH)—(CH$_2$)$_9$CH$_3$, preferably R$^1$ is —(CH$_2$)$_7$CH$_3$, or —CH$_2$CH(OH)—(CH$_2$)$_9$CH$_3$, more preferably R$^1$ is —(CH$_2$)$_7$CH$_3$.

Preferably, the weight ratio between the at least one, like one, preservative (P) and the isosorbide ether derivative(s) (IDE) [(P)/(IDE)] is from 0.1/1 to 10/1, more preferably from 1/1 to 8/1.

Typically the total amount of the isosorbide ether derivative (IED) according to formula (I) is in the range of 10 to 5000 ppm based on the total amount of the composition. In one embodiment of the invention the amount of the isosorbide ether derivative (IED) according to formula (I) is not more than 3000 ppm, preferably in the range of 10 to 3000 ppm, more preferably in the range of 10 to 2500 ppm, based on the total amount of the composition. In another embodiment of the invention the amount of the isosorbide ether derivative (IED) according to formula (I) is above 3000 ppm, preferably equal or above 3010 ppm, more preferably in the range of above 3000 to 50000 ppm, yet more preferably in the range of equal or above 3010 ppm to 5000 ppm, still more preferably in the range of 5000 to 40000 ppm. The latter embodiment is especially applicable in case the isosorbide ether derivative (IED) is not only used to enhance the storage stability or as a preservative (or preservative booster) but in addition as a thickener and/or emulsifier, and/or foam booster and/or sensory modifier and/or consistency factor and/or emollient, more preferably as thickener and/or emulsifier.

Further it might be possible that isosorbide ether (IE) or by-products (BP) not belonging to formula (I) might be present. However it is preferred that those compounds, namely isosorbide ether (IE) and by-products (BP) not belonging to formula (I), are present in minor amounts. Minor amounts according to this invention means that the amount is not more than 25 wt.-%, still more preferably not more than 15 wt.-%, yet more preferably not more than 10 wt.-%, still yet more preferably not more than 5.0 wt.-%, like not more than 3.0 wt.-%, e.g. not more than 2.0 wt.-% based on the total amounts of isosorbide ether derivatives, i.e. total amount of IED, BP and IE.

In a preferred embodiment the composition is a detergent or a cosmetic composition. Preferably the composition, e.g. the detergent or the cosmetic composition, is a liquid composition, like an aqueous composition.

Concerning definitions and further preferred embodiments, reference is made to the information under the heading "Use of the isosorbide ether derivative according to this invention as a preservative" or "Use of the isosorbide ether derivative according to this invention as a preservative booster".

In the following the invention is further described by way of examples.

EXAMPLES

The isosorbide alkylethers (compound (1) and (2)) can be prepared according to known etherification methods, e. g. as described in EP 2 295 030. The monoether can be purified by distillation. The hydroxyl ether derivatives (compound (3) and (4)) can be synthesized by reacting isosorbide with 1,2-alkyloxides as described in EP 2 174 941.

TABLE 1 monoether content

| | Monoether content/GC area % |
|---|---|
| Compound (1) | 91 |
| Compound (2) | 98 |

TABLE 1-continued monoether content

| | Monoether content/GC area % |
|---|---|
| Compound (3) | 82 |
| Compound (4) | 82 |

Compound (1) has the formula (I)

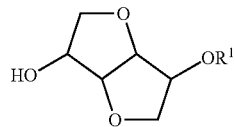

wherein
R$^1$ is —(CH$_2$)$_7$CH$_3$.

Compound (2) has the formula (I)

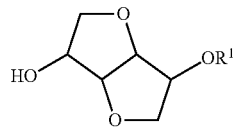

wherein
R$^1$ is —(CH$_2$)$_{11}$CH$_3$.
Compound (3) has the formula (I)

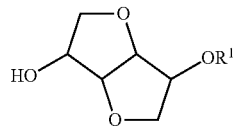

wherein
R$^1$ is —CH$_2$CH(OH)—(CH$_2$)$_7$CH$_3$.
Compound (4) has the formula (I)

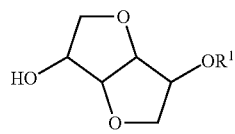

wherein
R$^1$ is —CH$_2$CH(OH)—(CH$_2$)$_9$CH$_3$.

Comparative compound (1) has the formula

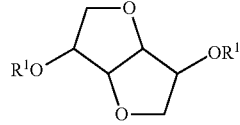

wherein
R$^1$ is —(CH$_2$)$_7$CH$_3$.

MIC:
Determination of Minimum Inhibitory Concentration (MIC) according to DIN 58 940

TABLE 2

| | MIC values | | | |
|---|---|---|---|---|
| | Compound (1) MIC [ppm] | Compound (2) MIC [ppm] | Compound (3) MIC [ppm] | Compound (4) MIC [ppm] |
| *Brevibacterium epidermis* | <500 | ≤20 | ≤200 | ≤20 |
| *Propionibacterium acnes* | <500 | ≤20 | <50 | <100 |
| *Staphylococcus aureus* | <500 | <50 | <500 | <100 |
| *Staphylococcus epidermis* | <100 | ≤20 | ≤20 | ≤20 |
| *Escherichia coli* | <1,000 | >10,000 | <2,000 | <2,000 |
| *Pseudomonas aeruginosa* | <1,000 | >10,000 | <1,000 | <1,000 |
| *Asperigillus brasiliensis* | <200 | ≤20 | <1000 | <200 |
| *Candida albicans* | <50 | ≤20 | ≤100 | ≤20 |
| *Malasse zia furfur* | <1,000 | 2,500 | ≤2500 | ≤20 |

TABLE 3

| | MIC values |
|---|---|
| | Comperative compound (1) MIC [ppm] |
| *Brevibacterium epidermis* | >10,000 |
| *Propionibacterium acnes* | >10,000 |
| *Staphylococcus aureus* | >10,000 |
| *Staphylococcus epidermis* | <200 |
| *Escherichia coli* | >10,000 |
| *Pseudomonas aeruginosa* | >10,000 |
| *Asperigillus brasiliensis* | >10,000 |
| *Candida albicans* | >10,000 |
| *Malasse zia furfur* | >10,000 |

The invention claimed is:
1. Composition comprising an isosorbide ether derivative (IED) of formula (I)

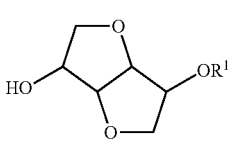

wherein
R$^1$ is —CH$_2$CH(OH)—R$^2$, wherein R$^2$ is a C$_6$ to C$_{10}$ n-alkyl residue.
2. Composition according to claim 1, wherein said composition comprises additionally a preservative (P) selected from the group consisting of formaldehyde, methylchloroisothiazolinone, methylisothiazolinone, benzoic acid including the salts thereof, bezoic acid esters, salicylic acid including the salts thereof, 4-hydroxy benzoic acid including the salts thereof, sorbic acid including the salts thereof, dehydroacetic acid including the salts thereof, dehydroacetic acid esters, phenoxyethanol, benzyl alcohol, 2-methylisothiazol-3(2H)-one, 4-isopropyl-m-cresol, and zinc pyrithione, wherein optionally a ratio between the preservative (P) and the isosorbide ether derivative (IDE) [(P)/(IDE)] is from 0.1/1 to 10/1.

3. Composition comprising
(a) an isosorbide ether derivative (IDE) of formula (I)

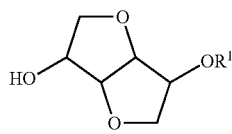

(I)

wherein
R$^1$ is —CH$_2$CH(OH)—R$^2$, wherein R$^2$ is a C$_6$ to C$_{10}$ n-alkyl residue, and
(b) a preservative (P) selected from the group consisting of formaldehyde, methylchloroisothiazolinone, methylisothiazolinone, benzoic acid including the salts thereof, bezoic acid esters, salicylic acid including the salts thereof, 4-hydroxy benzoic acid including the salts thereof, sorbic acid including the salts thereof, dehydroacetic acid including the salts thereof, dehydroacetic acid esters, phenoxyethanol, benzyl alcohol, 2-methylisothiazol-3(2H)-one, 4-isopropyl-m-cresol, and zinc pyrithione,
wherein the weight ratio between the preservative (P) and the isosorbide ether derivative (IDE) [(P)/(IDE)] is from 0.1/1 to 10/1.

4. Composition according to claim 3, wherein an amount of said isosorbide ether derivative (IED) in the composition does not exceed 3,000 ppm.

5. Composition according to claim 3, wherein R$^1$ of the isosorbide ether derivative (IED) according to formula (I) is —(CH$_2$)$_7$CH$_3$, —(CH$_2$)$_{11}$CH$_3$, —CH$_2$CH(OH)—(CH$_2$)$_7$CH$_3$, or —CH$_2$CH(OH)—(CH$_2$)$_9$CH$_3$.

6. Composition according to claim 3 being a liquid composition.

7. A method for improving a storage stability of a composition comprising adding to said composition, a composition comprising an isosorbide ether derivative (IED) of claim 1.

8. A method of preserving a composition comprising adding to said composition, a composition comprising an isosorbide ether derivative (IED) of claim 1.

9. The method according to claim 8, wherein said isosorbide ether derivative has a minimum inhibitory concentration (MIC) of not more than 3000 ppm.

10. The method according to claim 8, wherein said isosorbide ether derivative has a minimum inhibitory concentration (MIC) for
(a) gram positive bacteria of not more than 800 ppm; and/or
(b) gram negative bacteria of not more than 2500 ppm; and/or
(c) yeast and fungus of not more than 2500 ppm.

11. The method according to claim 8, wherein said isosorbide ether derivative has a minimum inhibitory concentration (MIC) for *Candica albicans* of not more than 100 ppm.

12. The method according to claim 8, wherein said isosorbide ether derivative is present in the composition in an amount of not more than 3000 ppm.

13. A method of enhancing the activity of a preservative comprising adding to said preservative a composition comprising an isosorbide ether derivative (IED) of claim 1.

14. The method according to claim 13, wherein the preservative is selected from the group consisting of formaldehyde, methylchloroisothiazolinone, methylisothiazolinone, benzoic acid including the salts thereof, bezoic acid esters, salicylic acid including the salts thereof, 4-hydroxy benzoic acid including the salts thereof, sorbic acid including the salts thereof, dehydroacetic acid including the salts thereof, dehydroacetic acid esters, phenoxyethanol, benzyl alcohol, 2-methylisothiazol-3(2H)-one, 4-isopropyl-m-cresol, and zinc pyrithione.

15. The method according to claim 8, wherein R$^1$ of the isosorbide ether derivative according to formula (I) is —(CH$_2$)$_7$CH$_3$, —(CH$_2$)$_{11}$CH$_3$, —CH$_2$CH(OH)—(CH$_2$)$_7$CH$_3$ or —CH$_2$CH(OH)—(CH$_2$)$_9$CH$_3$.

16. The method according to claim 8, wherein said composition comprising an isosorbide ether derivative (IED) is a liquid composition.

17. The method according to claim 8, wherein said composition is a detergent or a cosmetic composition.

18. The composition according to claim 1, wherein the amount of said isosorbide ether derivative (IED) in the composition does not exceed 3,000 ppm.

19. Composition according to claim 1 being a liquid composition.

* * * * *